(12) United States Patent
Kim

(10) Patent No.: US 9,364,189 B2
(45) Date of Patent: Jun. 14, 2016

(54) PORTABLE X-RAY IMAGE SYSTEM AND OPERATING TABLE USING THE SAME

(71) Applicant: NANOFOCUSRAY CO., LTD., Jeollabuk-do (KR)

(72) Inventor: Kyong Woo Kim, Jeollabuk-do (KR)

(73) Assignee: NANOFOCUSRAY CO., LTD., Jeollabuk-do (KR)

( * ) Notice: Subject to any disclaimer, the term of this patent is extended or adjusted under 35 U.S.C. 154(b) by 32 days.

(21) Appl. No.: 14/356,103

(22) PCT Filed: Oct. 1, 2013

(86) PCT No.: PCT/KR2013/008788
§ 371 (c)(1),
(2) Date: May 2, 2014

(87) PCT Pub. No.: WO2014/088193
PCT Pub. Date: Jun. 12, 2014

(65) Prior Publication Data
US 2015/0216493 A1 Aug. 6, 2015

(30) Foreign Application Priority Data

Dec. 3, 2012 (KR) .......................... 10-2012-0139250
Dec. 3, 2012 (KR) .......................... 10-2012-0139252

(51) Int. Cl.
*A61B 6/04* (2006.01)
*A61G 13/10* (2006.01)
(Continued)

(52) U.S. Cl.
CPC .............. *A61B 6/4441* (2013.01); *A61B 6/0407* (2013.01); *A61B 6/4405* (2013.01);
(Continued)

(58) Field of Classification Search
CPC ............ A61B 6/00; A61B 6/02; A61B 6/025; A61B 6/04; A61B 6/0407; A61B 6/0457; A61B 6/10; A61B 6/107; A61B 6/42; A61B 6/4283; A61B 6/44; A61B 6/4405; A61B 6/4411; A61B 6/4429; A61B 6/4435; A61B 6/4441; A61B 6/587; A61G 13/00; A61G 13/10; A61G 13/128; A61G 13/1285; A61G 2210/00; A61G 2210/50; G21F 1/00; G21F 1/02; G21F 1/08; G21F 1/085; G21F 1/125; G21F 3/00; A61N 5/10; A61N 5/1077; A61N 5/1081
USPC ............. 378/19, 20, 189, 193, 195–198, 204, 378/208–210; 250/491.1, 515.1, 517.1, 250/522.1; 5/600, 601
See application file for complete search history.

(56) References Cited

U.S. PATENT DOCUMENTS 3,158,742 A * 11/1964 Morel .................. A61B 6/0457
250/515.1
4,503,844 A * 3/1985 Siczek .................. A61G 13/00
5/11
(Continued)

FOREIGN PATENT DOCUMENTS

JP 11-197140 A 7/1999
JP 2003-260045 A 9/2003
(Continued)

OTHER PUBLICATIONS

Mark B. Williams et al., "Digital Radiography Image Quality: Image Acquisition", Journal of the American College of Radiology, Jun. 2007, pp. 371-388, vol. 4, No. 6.
(Continued)

*Primary Examiner* — Anastasia Midkiff
(74) *Attorney, Agent, or Firm* — Rabin & Berdo, P.C.

(57) ABSTRACT

Provided is an X-ray image photographing device, and more particularly, a portable X-ray image system available for multiple uses. In addition, disclosed is an X-ray image photographing device, and more particularly, an operating table which may be coupled to a portable X-ray image device.

12 Claims, 6 Drawing Sheets

(51) Int. Cl.
 A61B 6/10 (2006.01)
 A61B 6/00 (2006.01)
 A61G 13/12 (2006.01)
(52) U.S. Cl.
 CPC .............. *A61G13/128* (2013.01); *A61B 6/04* (2013.01); *A61B 6/107* (2013.01); *A61B 6/44* (2013.01); *A61B 6/4429* (2013.01); *A61B 6/4435* (2013.01); *A61G 13/10* (2013.01); *A61G 2210/50* (2013.01)

(56) References Cited

U.S. PATENT DOCUMENTS

| | | | | |
|---|---|---|---|---|
| 4,568,071 | A * | 2/1986 | Rice | A61B 6/0442 108/143 |
| 5,417,225 | A * | 5/1995 | Rubenstein | A71B 19/40 128/849 |
| 6,256,374 | B1 * | 7/2001 | Tomasetti | A61B 6/464 378/198 |
| 6,999,554 | B2 * | 2/2006 | Mertelmeier | A61B 6/502 378/196 |
| 8,046,054 | B2 | 10/2011 | Kim et al. | |
| 2005/0055772 | A1 * | 3/2005 | Maschke | A61B 6/04 5/601 |
| 2005/0152503 | A1 * | 7/2005 | Rauh | A61B 6/00 378/209 |
| 2006/0039537 | A1 * | 2/2006 | Strobel | A61B 6/032 378/197 |
| 2007/0140436 | A1 * | 6/2007 | Perry | A61B 6/4233 378/197 |
| 2007/0252095 | A1 * | 11/2007 | Magram | G21F 3/00 250/515.1 |
| 2008/0198973 | A1 * | 8/2008 | Timmermans | A61B 6/4441 378/197 |
| 2009/0046463 | A1 * | 2/2009 | Coombs | A61B 6/4405 362/253 |
| 2010/0249800 | A1 | 9/2010 | Kim et al. | |
| 2010/0266104 | A1 * | 10/2010 | Van Der Ende | A61B 6/4441 378/197 |
| 2011/0317816 | A1 * | 12/2011 | Bechard | A61B 6/00 378/98.8 |
| 2012/0224664 | A1 * | 9/2012 | Maack | A61B 6/02 378/7 |
| 2013/0301803 | A1 * | 11/2013 | Liu | A61B 6/42 378/114 |

FOREIGN PATENT DOCUMENTS

| | | |
|---|---|---|
| KR | 10-0731052 B1 | 6/2007 |
| KR | 10-0990474 B1 | 10/2010 |
| KR | 10-1194493 B1 | 10/2012 |

OTHER PUBLICATIONS

Edward J.C. Dawe et al., "A comparative study of radiation dose and screening time between mini C-arm and standard fluoroscopy in elective foot and ankle surgery", Foot and Ankle Surgery, 2011, pp. 33-36, vol. 17.
Brian D. Giordano et al., "Exposure to Direct and Scatter Radiation with Use of Mini-C-Arm Fluoroscopy", The Journal of Bone and Joint Surgery, 2007, pp. 948-952, vol. 89.
Brian D. Giordano et al., "Patient and Surgeon Radiation Exposure: Comparison of Standard and Mini-C-Arm Fluoroscopy", The Journal of Bone and Joint Surgery, 2009, pp. 297-304, vol. 91.
Brian L. Badman et al., "Radiation Exposure with Use of the Mini-C-Arm for Routine Orthopaedic Imaging Procedures", The Journal of Bone and Joint Surgery, 2005, pp. 13-17, vol. 87.
S. Sinha et al., "Radiation protection issues with the use of mini C-arm image intensifiers in surgery in the upper limb", The Journal of Bone and Joint Surgery, Apr. 2004, pp. 333-336, vol. 86-B, No. 3.

* cited by examiner

PORTABLE X-RAY IMAGE SYSTEM AND OPERATING TABLE USING THE SAME

TECHNICAL FIELD

The present disclosure relates to an X-ray image photographing device, and more particularly, to a portable X-ray image system available for multiple uses. In addition, the present disclosure relates to an X-ray image photographing device, and more particularly, to an operating table which may be coupled to a portable X-ray image device.

BACKGROUND ART

Generally, X-ray computerized tomography is installed within a limited number in a health care environment, and is also operated using a dedicated CT system, which is an expensive device located in a dedicated place in a health care facility, due to its size and weight. It is very unusual to find a CT system disposed in an operating room for the use in photographing during operation. Meanwhile, a C-arm type X-ray fluoroscopy system is a very inexpensive device frequently found in hospitals and medical offices, and generally has sufficient mobility so as to be used to a patient from a treatment point or an operating room.

A general C-arm is expensive and has a great size which has a limitation in space, and even though it is movable, the entire body of the C-arm should be moved, and thus the C-arm may not be easily used in an external environment.

In addition, the general C-arm has limitations in its functions and effects. In other words, the general C-arm may not perform radiography, fluoroscopy and tomosynthesis simultaneously. Here, the radiography means photographing in a vertical direction or in an oblique direction. The fluoroscopy means an inspection which emits X rays successively through a human body and photographs or observes the result through a monitor like a moving picture, and if necessary, obtains an accurate image of an interested region by using a barium colloidal suspension or a contrast medium through which X rays may not easily pass. The fluoroscopy is used during surgical procedures or operations. The tomosynthesis is used for obtaining a 3D image by emitting X rays while rotating an X-ray tube within a limited angle, and is frequently applied to a breast photographing device or a chest photographing device.

In addition, the general C-arm is very expensive and has a very great size in comparison to a C-arm capable of only 2D images, even though it may contain 3D images.

As a background art, there are patent literatures in relation to an operating system for an imaging device, and an imaging device having a curved arm is disclosed.

DISCLOSURE

Technical Problem

The present disclosure is directed to proposing an operating table which allows a surgical procedure using a small portable X-ray image device which may be carried by a user and support multiple functions.

The present disclosure is also directed to proposing a portable X-ray image device which may be carried by a user and used in multiple purposes, even for radiography, fluoroscopy and tomosynthesis.

In addition, the present disclosure is directed to proposing an operating table which allows a surgical procedure using a small portable X-ray image device which may be carried by a user and support multiple functions.

Technical Solution

In one general aspect, there is provided a portable X-ray image system.

The portable X-ray image system according to an embodiment of the present disclosure includes a portable X-ray image device 100 having a C shape and also having an X-ray tube 10 and an X-ray detector 20 at both ends of a body 30, respectively, and the X-ray detector 20 detects X rays generated from the X-ray tube 10 to obtain an X-ray image, a photographing target being located between the X-ray tube 10 and the X-ray detector 20 to allow X-ray photographing.

The X-ray tube 10 is rotatable within a preset angle range.

The body 30 includes a first body 31 and a second body 32, wherein the first body 31 is coupled and fixed to the X-ray tube 10, and the second body 32 is coupled and fixed to the X-ray detector 20. The first body 31 and the second body 32 are pivotally coupled.

The portable X-ray image device 100 may further include a clutch installed between the first body 31 and the second body 32, and the X-ray tube 10 may rotate when the clutch is released.

The X-ray detector 20 may include a detection module 21 movable therein.

The X-ray detector 20 may further include a shaft, a ball screw and a motor for the movement of the detection module 21.

The X-ray detector 20 may further include threes sensors for detecting a center and both ends of the X-ray detector 20.

The portable X-ray image system may further include a stand 200 coupled to the portable X-ray image device 100, and the stand 200 may include: a base 220 having a wheel 221; and a support 210 coupled to the portable X-ray image device 100.

The portable X-ray image device 100 coupled to the stand 200 may rotate in 360 degrees and be coupled to the support 210 to move along the support 210 or protrude from the support 210.

The portable X-ray image device 100 may further include a battery contained therein or detachably attached to an outside thereof.

In another aspect of the present disclosure, there is provided an operating table coupled to the portable X-ray image device 100.

The operating table according to an embodiment of the present disclosure includes: an operating table body 310 having an insert 340 in which an X-ray detector 20 of the portable X-ray image device 100 is inserted and movable therein; a shielding cover 320 installed along an upper rim of the operating table body 310; and an operating table cover 330 located above the operating table body 310 and to cover the insert 340 and allow an operating target to be placed thereon.

The insert 340 may include a moving unit for moving the portable X-ray image device 100.

The moving unit may include: a shaft 341 installed along a preset moving path; and a conveying plate 342 coupled to the shaft 341 to move along the shaft 341.

The conveying plate 342 may have a '⊂' shape at which the X-ray detector 20 is placed, and the conveying plate 342 may further include an anti-separation plate 343 for preventing the portable X-ray image device 100, coupled thereto, from being separated.

The conveying plate 342 may further include a guide unit 344 for guiding the X-ray detector 20 to be stably placed.

The shielding cover 320 may have a hole 321 formed to allow a hand of an operator to be inserted therein for an internal work.

The shielding cover 320 may shield X rays generated from the portable X-ray image device 100 and be made of transparent material to allow an operator to check an internal state.

The operating table cover 330 may be made of X-ray transmitting material so that the X-ray detector 20 detects X rays.

Advantageous Effects

The present disclosure allows a surgical procedure using a portable X-ray image device which may be carried by a user and support multiple functions.

BEST MODE

Figure 1:
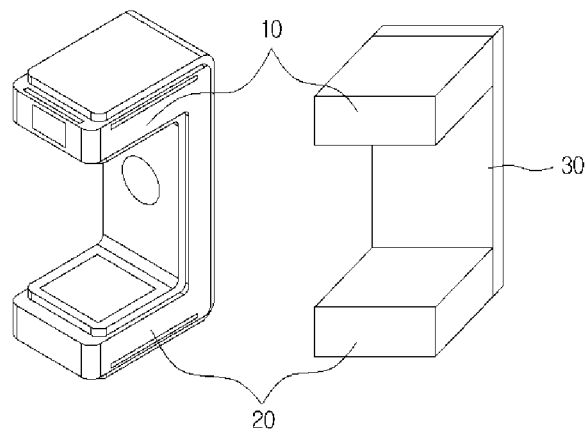
FIG. 1 is a diagram showing a portable X-ray image device.

Since the present disclosure may be modified in various ways and have various embodiments, specific embodiments will be depicted in the drawings and described in details therein. However, the present disclosure is not limited to specific embodiments, and all modifications, equivalents and replacements included in the scope of the present disclosure should be understood as falling within the present disclosure.

In the description, details of well-known features and techniques may be omitted to avoid unnecessarily obscuring the presented embodiments. In addition, numbers used in describing the present disclosure (for example, first, second or the like) are just discernment signs for distinguishing any element from other elements.

Moreover, if it is mentioned in the specification that any component "is connected to" or "accesses" another component, it should be understood that any component may not only be directly connected to or access another component but also may be connected to or access another component via any other component, as long as it is not stated otherwise.

Hereinafter, an embodiment of the present disclosure will be described in detail with reference to the accompanying drawings. In the description of the present disclosure, like numerals denote like elements for better understanding.

Figure 2:
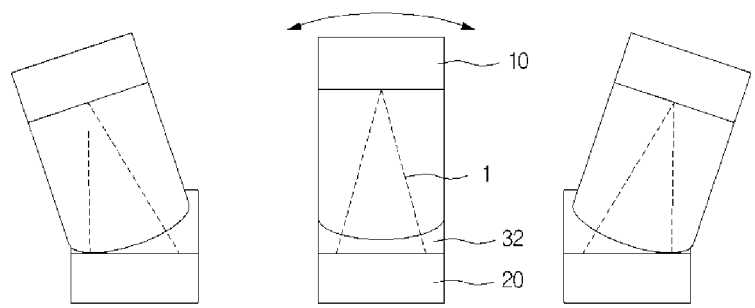
FIGS. 2 and 3 are diagrams for illustrating operations of the portable X-ray image device.
Figure 2:
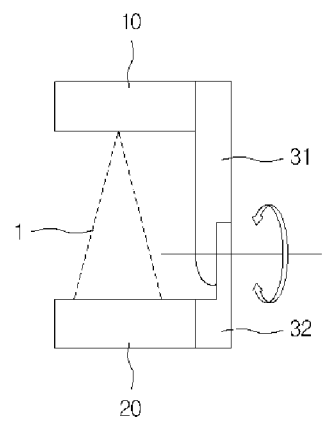
Figure 3:
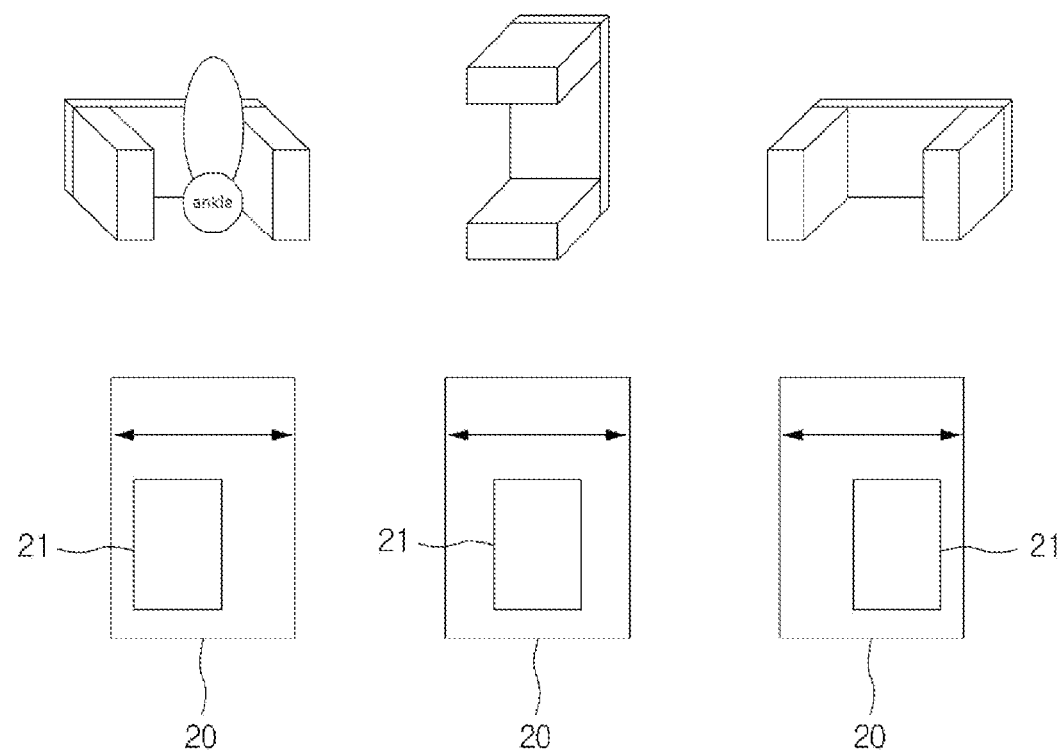
Figure 4:
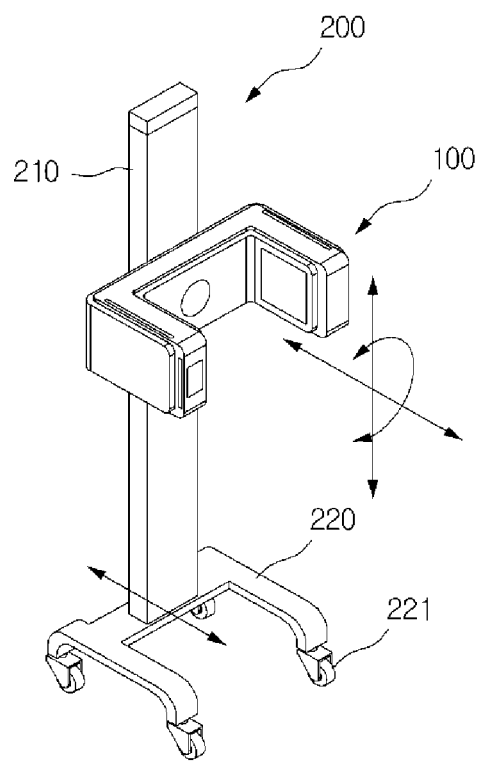
FIG. 4 is a diagram showing a stand coupled to the portable X-ray image device.
Figure 5:
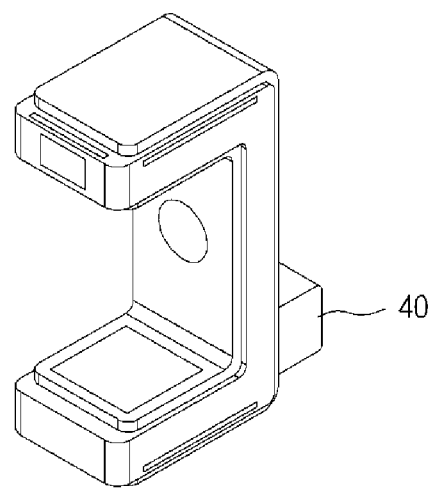
FIG. 5 is a diagram showing a portable X-ray image device to which a battery is mounted.

FIG. 1 is a diagram showing a portable X-ray image device, FIGS. 2 and 3 are diagrams for illustrating operations of the portable X-ray image device, FIG. 4 is a diagram showing a stand coupled to the portable X-ray image device, and FIG. 5 is a diagram showing a portable X-ray image device to which a battery is mounted.

Hereinafter, a portable X-ray image device according to an embodiment of the present disclosure will be described with reference to FIGS. 1 to 5.

First, referring to FIG. 1, a portable X-ray image device 100 has a C shape and includes an X-ray tube 10 and an X-ray detector 20 at both ends of a body 30, respectively.

The X-ray tube 10 is an X-ray generator, and the X-ray detector 20 detects X rays generated from the X-ray tube 10 to obtain an X-ray image. For example, a photographing target may be located between the X-ray tube 10 and the X-ray detector 20 to allow X-ray photographing.

The portable X-ray image device 100 may partially rotate for the tomosynthesis imaging.

For example, as shown in FIG. 2, the body 30 of a small portable X-ray image device 100 (or, an arm) may be composed of a first body 31 and a second body 32. In other words, the first body 31 may be coupled and fixed to the X-ray tube 10, and the second body 32 may be coupled and fixed to the X-ray detector 20. In addition, the first body 31 and the second body 32 may be pivotally coupled. Accordingly, in a state where the X-ray detector 20 is fixed, the X-ray tube 10 may irradiate X rays 1 to a photographing target while rotating, so that a side or an oblique section of the photographing target may be photographed. In addition, any interference of equipment during operations may also be prevented.

In addition, the portable X-ray image device 100 may rotate manually or automatically. In case of automatic rotation, a gear or belt may be used to transmit a rotating force of a motor to implement a rotating motion. In case of manual rotation, a clutch may be installed between the first body 31 and the second body 32 so that the X-ray tube 10 may rotate when the clutch is released.

The X-ray detector 20 of the portable X-ray image device 100 contains a detection module 21 rotatable therein.

For example, as shown in FIG. 3, if a photographing target located between the X-ray tube 10 and the X-ray detector 20 is an ankle, the photographing target may not be located at a proper position, for example a geographical center of the X-ray detector 20. In this case, for accurate photographing, the detection module 21 may be moved right and left, without moving the photographing target.

As described above, shafts (or, LM guides) may be installed at both sides of the X-ray detector 20 in order to move the detection module 21, a ball screw for moving the detection module 21 may be installed, and a motor may also be installed at the ball screw. In addition, three sensors may be installed to detect a center and both ends of the X-ray detector 20. Therefore, if it is needed to move the detection module 21, the detection module 21 may be moved to the center or any end by the input of a user or a specific program.

In addition, the X-ray detector 20 determines by using a sensor such as a tilt angle sensor whether the detection module 21 needs to be moved, and if movement is required, the detection module 21 may be moved.

The portable X-ray image system according to an embodiment of the present disclosure may further include a stand 200.

For example, as shown in FIG. 4, the portable X-ray image device 100 may be coupled to the stand 200. In other words, the stand 200 may include a base 220 having a wheel 221 and a support 210 coupled to the portable X-ray image device 100. Here, the portable X-ray image device 100 may rotate in 360 degrees and be coupled to the support 210 to move along the support 210 or protrude from the support 210.

In addition, the stand 200 may further include a battery and a unit for controlling an operation or steering of the wheel.

Moreover, a camera may be separately attached to the stand 200 so that if a photographing position of a patient is input, the stand 200 may automatically move to the photographing position. The stand 200 may also have a function of automatically stopping when the stand 200 reaches a photographing position or a contact or external force over a certain level occurs (for example, when the stand 200 collides with a patient).

In addition, the stand 200 may further include a clutch between the portable X-ray image device 100 and the stand 200 so that the portable X-ray image device 100 may be manually rotated according to the manipulation of a user. The portable X-ray image device 100 may rotate successively, and the portable X-ray image device 100 and the stand 200 may be coupled so that they recover an original state after rotating in 360 degrees during CT photographing.

The portable X-ray image device 100 may include a small PC therein to perform various functions for such as equipment control, image processing or the like, and may also have a communication function for communicating with the outside, particularly a portable terminal such as a smart phone. In this case, a user may control the portable X-ray image device 100 by using a portable terminal and check a photographed image in real time.

In addition, the small portable X-ray image device 100 may include a battery contained therein or a battery 40 attached to an outside thereof as shown in FIG. 5. Here, the battery 40 may be detachably attached to an outer case of the portable X-ray image device 100 and may also be used as a power source of the portable X-ray image device 100 or a power source of the stand 200.

Figure 6:
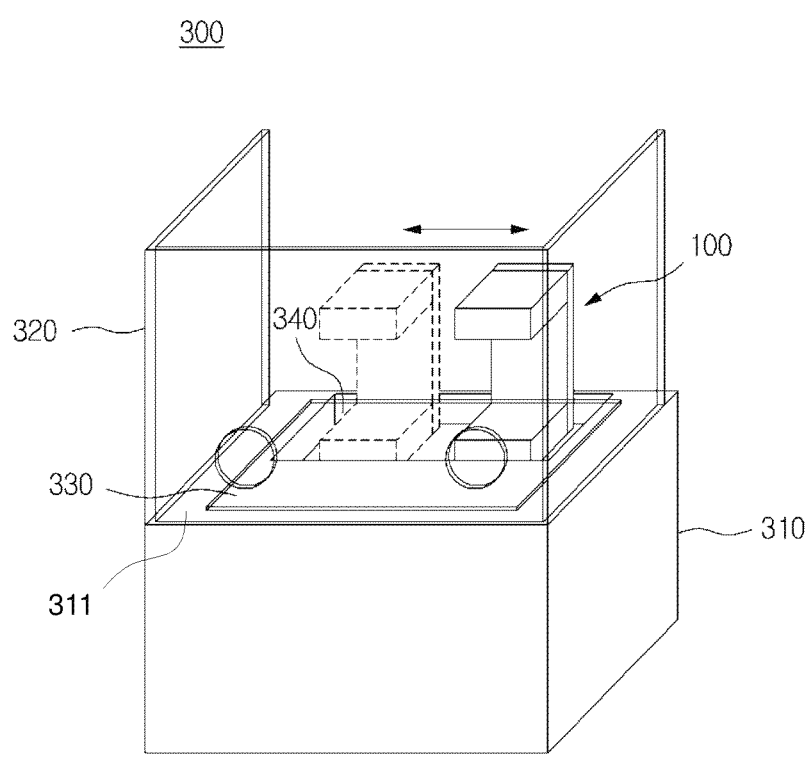
FIG. 6 is a diagram showing an operating table having a small portable X-ray image device.
Figure 7:
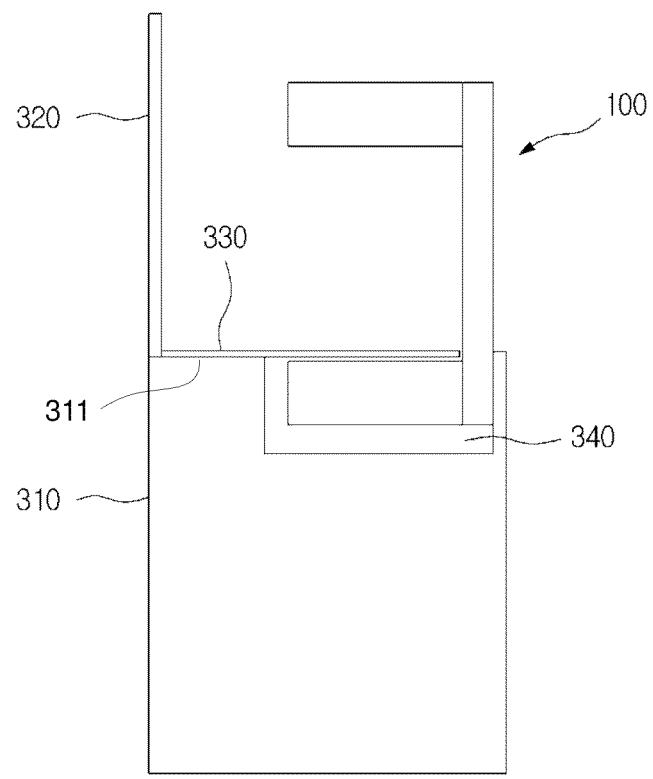
FIG. 7 is a side view showing the operating table of FIG. 6.
Figure 8:
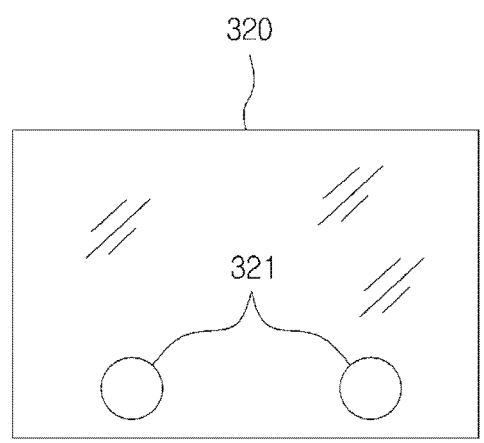
FIG. 8 is a diagram showing a shielding cover of the operating table.
Figure 9:
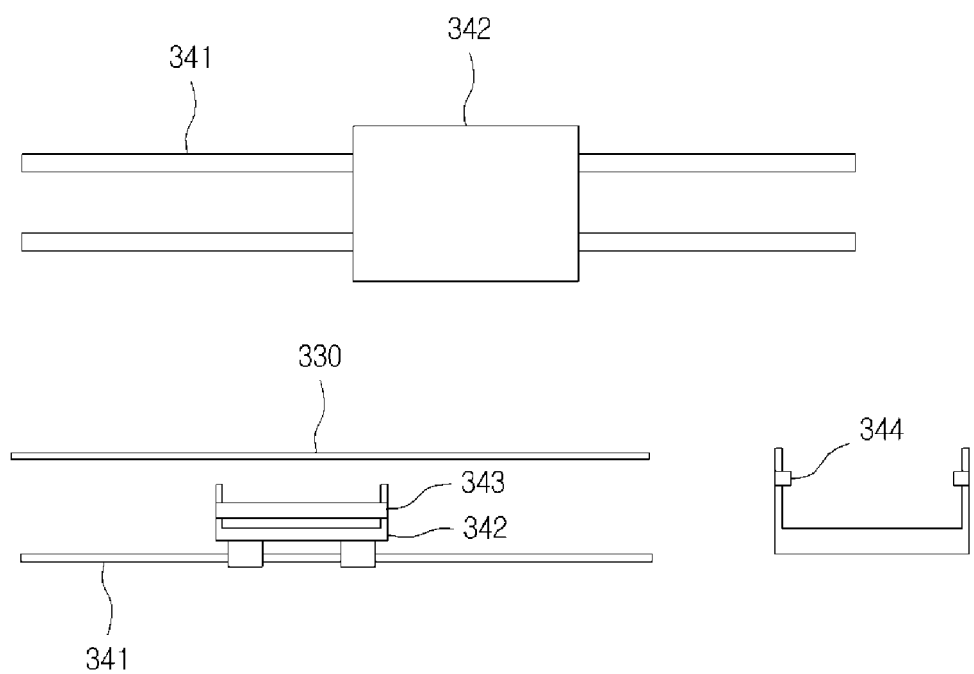
FIG. 9 is a diagram showing a moving unit of the small portable X-ray image device employed in the operating table.

FIG. 6 is a diagram showing an operating table having a small portable X-ray image device, FIG. 7 is a side view showing the operating table of FIG. 6, FIG. 8 is a diagram showing a shielding cover of the operating table, and FIG. 9 is a diagram showing a moving unit of the small portable X-ray image device employed in the operating table.

Hereinafter, the operating table will be described with reference to FIGS. 6 and 7 basically, and FIGS. 8 and 9 will also be referred to.

Referring to FIGS. 6 and 7, the operating table 300 includes an operating table body 310, a shielding cover 320 and an operating table cover 330.

The operating table body 310 has an insert 340 in a top plate 311 thereof, and the X-ray detector 20 of the portable X-ray image device 100 may be inserted into the insert 340 and movable therein.

The shielding cover 320 shields X rays generated from the portable X-ray image device 100 to minimize the exposure to radiation, and as shown in FIGS. 6 and 7, the shielding cover 320 may be installed along an upper rim of the operating table body 310. For example, the shielding cover 320 may have a pair of holes 321 through which hands of an operator may be inserted for an internal work, as shown in FIG. 8, and the shielding cover 320 may be made of transparent material such as lead glass, transparent lead, acryl or the like so that the operator may check an internal state.

The operating table cover 330 gives a place on which an operating target may be placed, and as shown in FIGS. 6 and 7, the operating table cover 330 is located above the operating table body 310 and covers the insert 340. By doing so, the operating target may be located between the X-ray tube 10 and the X-ray detector 20 of the portable X-ray image device 100 for X-ray photographing. For example, the operating table cover 330 may be made of X-ray transmitting material such as acryl, carbon plate or the like so that the X-ray detector 20 may detect X rays.

The insert 340 formed at the operating table body 310 gives a space in which the X-ray detector 20 is inserted and moves and includes a moving unit for moving the portable X-ray image device 100.

For example, as shown in FIG. 9, the moving unit of the portable X-ray image device 100 may include a pair of shafts (LM guides) 341 installed along a preset moving path and conveying plates 342 coupled to the shafts 341 to move along the shafts 341. The conveying plate 342 may have a '⊂' shape so that the X-ray detector 20 of the portable X-ray image device 100 may be placed thereat, and the conveying plate 342 may further include an anti-separation plate 343 for preventing the portable X-ray image device 100, coupled thereto, from being separated. In addition, the conveying plate 342 may further include a guide unit 344 for guiding the X-ray detector 20 of the portable X-ray image device 100 to be stably placed.

For example, if the movement of the conveying plate 342 is automatically controlled, a ball screw may be installed instead of the shaft 341 so that the movement of the conveying plate 342 is controlled using a motor.

The present disclosure has been described in detail. However, it should be understood that the detailed description and specific examples, while indicating preferred embodiments of the disclosure, are given by way of illustration only, since various changes and modifications within the spirit and scope of the disclosure will become apparent to those skilled in the art from this detailed description.

What is claimed is:

1. An operating table, which is coupled to a portable X-ray image device, the operating table comprising:
    an operating table body having an insert in which an X-ray detector of the portable X-ray image device is inserted and movable therein;
    a shielding cover installed along an upper rim of the operating table body; and
    an operating table cover located above the operating table body and to cover the insert and allow an operating target to be placed thereon,
    wherein the insert includes a moving unit for moving the portable X-ray image device, the moving unit including a shaft installed along a preset moving path, and
    a conveying plate coupled to the shaft to move along the shaft, and
    wherein the conveying plate has a '⊂' shape at which the X-ray detector is placed, and the conveying plate further includes an anti-separation plate for preventing the portable X-ray image device from being separated from the conveying plate.

2. The operating table according to claim 1, wherein the conveying plate further includes a guide unit for guiding the X-ray detector to be stably placed.

3. The operating table according to claim 1, wherein the shielding cover has a hole formed to allow a hand of an operator to be inserted therein for an internal work.

4. The operating table according to claim 1, wherein the shielding cover shields X rays generated from the portable X-ray image device and is made of transparent material to allow an operator to check an internal state.

5. The operating table according to claim 1, wherein the operating table cover is made of X-ray transmitting material so that the X-ray detector detects X rays.

6. A portable X-ray image system comprising:
    an operating table body including
        a top plate disposed on a top end of the operating table body, and
        an insertion hole formed in the top plate;
    a portable X-ray image device including
        an X-ray body,
        an X-ray tube disposed in a first end of the X-ray body and configured to irradiate X-rays, and an X-ray detector disposed in a second end of the X-ray body and configured to detect the X-rays,
wherein the X-ray body of the portable X-ray image device is inserted into the insertion hole such that the X-ray tube is disposed above the top plate and the X-ray detector is disposed under the top plate;
an operating table cover disposed on the top plate and covering the top plate and a part or whole part of the insertion hole;
a shielding cover installed on the top plate along an upper rim of the operating table body.

7. The portable X-ray image system according to claim 6, further comprising
a moving unit for moving the portable X-ray image devcie, the moving unit including
a shaft disposed under the top plate, and
a conveying plate moving along the shaft.

8. The portable X-ray image system according to claim 7, wherein the conveying plate has a '⊂' shape at which the X-ray detector is placed, and includes an anti-separation plate for preventing the portable X-ray image device from being separated from the conveying plate.

9. The portable X-ray image system according to claim 8, wherein the conveying plate further includes a guide unit for guiding the X-ray detector to be stably placed.

10. The portable X-ray image system according to claim 6, wherein the shielding cover has one or more holes formed to allow a hand of an operator to be inserted therein for an internal work.

11. The portable X-ray image system according to claim 6, wherein the shielding cover shields the X-rays generated from the portable X-ray image device and is made of transparent material to allow an operator to check an internal state.

12. The portable X-ray image system according to claim 6, wherein the operating table cover is made of an X-ray transmitting material so that the X-ray detector detects the X-rays.

* * * * *